(12) United States Patent
Abdel-Meguid et al.

(10) Patent No.: US 9,682,085 B2
(45) Date of Patent: Jun. 20, 2017

(54) ANTI-PROPROTEIN CONVERTASE SUBTILISIN KEXIN TYPE 9 (ANTI-PCSK9) COMPOUNDS AND METHODS OF USING THE SAME IN THE TREATMENT AND/OR PREVENTION OF CARDIOVASCULAR DISEASES

(71) Applicant: Shifa Biomedical Corporation, Malvern, PA (US)

(72) Inventors: Sherin Salaheldin Abdel-Meguid, Exton, PA (US); Nabil Elshourbagy, Chester, PA (US); Harold Meyers, Weston, PA (US); Shaker A. Mousa, Wynantskill, NY (US)

(73) Assignee: Shifa Biomedical Corporation, Malvern, PA (US)

( * ) Notice: Subject to any disclaimer, the term of this patent is extended or adjusted under 35 U.S.C. 154(b) by 0 days.

(21) Appl. No.: 14/767,133

(22) PCT Filed: Mar. 11, 2014

(86) PCT No.: PCT/US2014/022957
§ 371 (c)(1),
(2) Date: Aug. 11, 2015

(87) PCT Pub. No.: WO2014/150326
PCT Pub. Date: Sep. 25, 2014

(65) Prior Publication Data
US 2015/0374710 A1    Dec. 31, 2015

Related U.S. Application Data

(60) Provisional application No. 61/788,061, filed on Mar. 15, 2013.

(51) Int. Cl.
| | |
|---|---|
| *A61K 31/5377* | (2006.01) |
| *A61K 31/4015* | (2006.01) |
| *A61K 31/4439* | (2006.01) |
| *A61K 31/433* | (2006.01) |
| *A61K 31/42* | (2006.01) |
| *A61K 31/4196* | (2006.01) |
| *A61K 31/426* | (2006.01) |
| *A61K 31/404* | (2006.01) |
| *A61K 31/4155* | (2006.01) |
| *A61K 31/415* | (2006.01) |
| *A61K 31/4545* | (2006.01) |
| *A61K 31/4178* | (2006.01) |

(52) U.S. Cl.
CPC ........ *A61K 31/5377* (2013.01); *A61K 31/404* (2013.01); *A61K 31/415* (2013.01); *A61K 31/4155* (2013.01); *A61K 31/4178* (2013.01); *A61K 31/4196* (2013.01); *A61K 31/42* (2013.01); *A61K 31/426* (2013.01); *A61K 31/433* (2013.01); *A61K 31/4439* (2013.01); *A61K 31/4545* (2013.01); *A61K 31/4015* (2013.01)

(58) Field of Classification Search
CPC ............ A61K 31/5377; A61K 31/4015; A61K 31/4439
See application file for complete search history.

(56) References Cited

U.S. PATENT DOCUMENTS

| | | | |
|---|---|---|---|
| 4,017,313 A | 4/1977 | Hartzler | |
| 4,371,607 A | 2/1983 | Donges | |
| 8,003,654 B2 | 8/2011 | Aissaoui | |
| 2003/0149081 A1* | 8/2003 | Zou | A61K 31/4015 514/343 |
| 2008/0090829 A1 | 4/2008 | Hamanaka | |
| 2009/0226422 A1* | 9/2009 | Chaudhary | A01K 67/0271 424/130.1 |
| 2009/0275053 A1 | 11/2009 | Horton et al. | |
| 2010/0184730 A1 | 7/2010 | Vu et al. | |
| 2010/0233177 A1 | 9/2010 | Yowe et al. | |
| 2011/0009628 A1 | 1/2011 | Liu et al. | |
| 2012/0252796 A1 | 10/2012 | Pingali et al. | |
| 2014/0093513 A1 | 4/2014 | Milne et al. | |
| 2014/0099333 A1 | 4/2014 | Schwink et al. | |

OTHER PUBLICATIONS

Santos et al. The Lancet, 2014, vol. 385, No. 9965, pp. 307-310.*
Xu et al. J. Med. Chem., 2011, vol. 54, pp. 7567-7578.*
Abifadel, Marianne et al., "Mutations in PCSK9 cause autosomal dominant hypercholesterolemia", Nature Genetics, 34(2): 154-156 (2003).
Benjannet, Suzanne et al., "The Proprotein Convertase (PC) PCSK9 Is Inactivated by Furin and/or PC5/6A", Journal of Biological Chemistry, 281(41): 30561-30572 (2006).
Benjannet, Suzanne et al., "NARC-1/PCSK9 and Its Natural Mutants", The Journal of Biological Chemistry, 279 (47): 48865-48875 (2004).
Bottomley, Matthew J. et al., "Structural and Biochemical Characterization of the Wild Type PCSK9-EGF (AB) Complex and Natural Familial Hypercholesterolemia Mutants", Journal of Biological Chemistry, 284(2): 1313-1323 (2009).
Cohen, Jonathan et al., "Low LDL cholesterol in individuals of African descent resulting from frequent nonsense mutations in PCSK9", Nature Genetics, 37(2): 161-165 (2005).
Crunkhorn, Sarah, "PCSK9 antibody reduces LDL cholesterol", Nature Reviews/Drug Discovery, 11: 11 (2012).
Cunningham, David et al., "Structural and biophysical studies of PCSK9 and its mutants linked to familial hypercholesterolemia", Nature Structural & Molecular Biology, 14(5): 413-419 (2007).

(Continued)

*Primary Examiner* — Samira Jean-Louis
(74) *Attorney, Agent, or Firm* — Patrick J. Hagan; Dann, Dorfman, Herrell and Skillman

(57) ABSTRACT

Disclosed are compounds that modulate the physiological action of the proprotein convertase subtilisin kexin type 9 (PCSK9), as well as therapeutic methods for use of such compounds to reduce LDL-cholesterol levels and/or for the treatment and/or prevention of cardiovascular disease (CVD), including treatment of hypercholesterolemia. Examples of compounds include thiadiazole, isoxazole, 1,2, 4-triazole, thiazole, indole, pyrazole, and pyrrolinone derivatives.

5 Claims, 11 Drawing Sheets

(56) References Cited

OTHER PUBLICATIONS

Frank-Kamenetsky, Maria et al., "Therapeutic RNAi targeting PCSK9 acutely lowers plasma cholesterol in rodents and LDL cholesterol in nonhuman primates", PNAS, 105(33): 11915-11920 (2008).
Graham, Mark J. et al., "Antisense inhibition of proprotein convertase subtilisin/kexin type 9 reduces serum LDL in hyperlipidemic mice", Journal of Lipid Research, 48: 763-767 (2007).
Grundy, Scott M. et al., "Implications of Recent Clinical Trials for the National Cholesterol Education Program Adult Treatment Panel III Guidelines", Circulation, 110: 227-239 (2004).
Kwon, Hyock Joo et al., "Molecular basis for LDL receptor recognition by PCSK9", PNAS, 105(6): 1820-1825 (2008).
Li, Jun et al., "Secreted PCSK9 promotes LDL receptor degradation independently of proteolytic activity", Biochem. J., 406: 203-207 (2007).
Maxwell, Kara N. et al., "Adenoviral-mediated expression of PCSK9 in mice results in a low-density lipoprotein receptor knockout phenotype", PNAS, 101(18): 7100-7105 (2004).
McNutt, Markey et al., "Antagonism of Secreted PCSK9 Increases Low Density Lipoprotein Receptor Expression in HepG2 Cells", The Journal of Biological Chemistry, 284(16): 10561-10570 (2009).
McNutt, Markey et al., "Catalytic Activity if Not Required for Secreted PCSK9 to Reduce Low Density Lipoprotein Receptors in HepG2 Cells", Journal of Biological Chemistry, 282(29): 20799-20803 (2007).
Piper, Derek E. et al., "The Crystal Structure of PCSK9: A Regulator of Plasma LDL-Cholesterol", Structure, 15: 545-552 (2007).
Rashid, Shirya et al., "Decreased plasma cholesterol and hypersensitivity to statins in mice lacking PCSK9", PNAS, 102(15): 5374-5379 (2005).
Seidah, Nabil G. et al., "The secretory proprotein convertase neural apoptosis-regulated convertase 1 (NARC-1): Liver recognition and neuronal differentiation", PNAS, 100(3): 928-933 (2003).
Swergold, Gary et al., Core 2. Epidemiology and Prevention of CV Disease: Physiology, Pharmacology and Lifestyle, Circulation, 122: A23251 (2010).
Zhang, Da Wei et al., "Binding of Proprotein Convertase Subtilisin/Kexin Type 9 to Epidermal Growth Factor-like Repeat A of Low Density Lipoprotein Receptor Decreases Receptor Recycling and Increases Degradation", Journal of Biological Chemistry, 282(25): 18602-18612 (2007).
Zhao, Zhenze et al., "Molecular Characterization of Loss-of-Function Mutations in PCSK9 and Identification of a Compound heterozygote", The American Journal of Human Genetics, 79: 514-523 (2006).
Amgen, "Ascending Multiple Dose Study to Evaluate the Safety, Tolerability, Pharmacokinetics and Pharmacodynamics of Evolocumab (AMG 145) in Adults with Hyperlipidemia on Stable Doses of a Statin", ClinicalTrials.gov (2010).
International Serach Report/Written Opinion, dated Aug. 29, 2014, issued in corresponding International Application No. PCT/US2014/022957, filed Mar. 11, 2014.
Pisciotta, Livia et al., "Additive effect of mutations in LDLR and PCSK9 genes on the phenotype of familial hypercholesterolemia", Atherosclerosis, 186: 433-440 (2006).
International Serach Report/Written Opinion, dated Aug. 13, 2014, issued in corresponding International Application No. PCT/US2014/023135, filed Mar. 11, 2014.
Yangthara, Buranee et al., "Small-Molecule Vasopressin-2 Receptor Antagonist Identified by a G-Protein Coupled Receptor Pathway Screen", Molecular Pharmacology, 72(1): 86-94 (2007).
Extended European Search Report, dated Aug. 8, 2016, issued in corresponding European Application No. 14770138.7, filed Mar. 11, 2014.

* cited by examiner

| Group | Treatment Groups |
|---|---|
| 1 | Regular diet control group -- Vehicle (SC, QD) |
| 2 | High fat-diet control group -- Vehicle (SC, DQ) |
| 3 | High fat-diet reference group -- Atorvastatin (40 mg/Kg, SC, QD) |
| 4 | High fat-diet group -- SBC-115,076 (4 mg/kg, SC, QD) |
| 5 | High fat-diet group -- SBC-110,034 (4 mg/kg, SC, QD) |

FIGURE 7

| Treatment | Cholesterol (mg/dl) | | | | | | | | |
|---|---|---|---|---|---|---|---|---|---|
| | A1 | A2 | A3 | A4 | A5 | A6 | A7 | A8 | Mean |
| HFD after 9 Weeks + Vehicle (Week 2) | 223.5 | 236.3 | 226.7 | 226.7 | 255.4 | 214.0 | 220.4 | 233.1 | 229.5 |
| HFD + SBC-115,076 (4mg/kg, SC daily 7 days) | 191.7 | 198.1 | 137.6 | 166.2 | 169.4 | 182.1 | 143.9 | 124.8 | 164.2 |
| HFD + SBC-115,076 (4mg/kg, SC daily 14 days) | 163.0 | 194.9 | 163.0 | 179.0 | 124.8 | 166.2 | 143.9 | 115.3 | 156.3 |
| | Mean % Reduction of Cholesterol Levels | | | | | | | | 32% |
| HFD after 9 Weeks + Vehicle (Week3) | 227 | 211 | 226 | 244 | 204 | 214 | 218 | 210 | 219 |
| Atorvastatin 40 mg/Kg, SC daily (Week3) | 152 | 182 | 176 | 158 | 152 | 158 | 142 | 156 | 160 |
| | Mean % Reduction of Cholesterol Levels | | | | | | | | 27% |
| Regular Diet Animals | 85.3 | 88.1 | 90.1 | 80.3 | 86.6 | 78.2 | 82.3 | 92.4 | 85.4 |

FIGURE 8

ANTI-PROPROTEIN CONVERTASE SUBTILISIN KEXIN TYPE 9 (ANTI-PCSK9) COMPOUNDS AND METHODS OF USING THE SAME IN THE TREATMENT AND/OR PREVENTION OF CARDIOVASCULAR DISEASES

CROSS-REFERENCE TO RELATED APPLICATIONS

This application is a 371 of International Application No. PCT/US2014/022957, filed Mar. 11, 2014, which claims the benefit of U.S. Provisional Patent Application No. 61/788,061, filed Mar. 15, 2013, the entire disclosure of each of the aforesaid applications is incorporated by reference in the present application.

STATEMENT REGARDING FEDERAL SPONSORED RESEARCH OR DEVELOPMENT

The present invention was made with support from the National Heart, Lung and Blood Institute (NHLBI) under SBIR Grant No. 1R43HL096167-01. The U.S. Government has certain rights in this invention.

FIELD OF INVENTION

The present invention relates to compounds that modulate the physiological action of the proprotein convertase subtilisin kexin type 9 (PCSK9), including its interaction with the low density lipoprotein receptor (LDLR). More specifically, the invention relates to compositions comprising small molecule modulators of PCSK9 function and methods of using these modulators as a medicament. The small molecule modulators of PCSK9 function can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

BACKGROUND OF INVENTION

Cardiovascular diseases are the leading cause of death, with atherosclerosis being the leading cause of cardiovascular diseases. Atherosclerosis is a disease of the arteries and is responsible for coronary heart disease associated with many deaths in industrialized countries. Several risk factors for coronary heart disease have now been identified: dyslipidemia, hypertension, diabetes, smoking, poor diet, inactivity and stress. Dyslipidemia is elevation of plasma cholesterol (hypercholesterolemia) and/or triglycerides (TGs) or a low high-density lipoprotein (HDL) level that contributes to the development of atherosclerosis. It is a metabolic disorder that is proven to contribute to cardiovascular disease. In the blood, cholesterol is transported in lipoprotein particles, where the low-density lipoprotein (LDL) cholesterol (LDL-C) is considered "bad" cholesterol, while HDL-cholesterol (HDL-C) is known as "good" cholesterol. Lipid and lipoprotein abnormalities are extremely common in the general population and are regarded as a highly modifiable risk factor for cardiovascular disease, due to the influence of cholesterol on atherosclerosis. There is a long-felt significant unmet need with respect to CVD with 60-70% of cardiovascular events, heart attacks and strokes occurring despite the treatment with statins (the current standard of care in atherosclerosis). Moreover, new guidelines suggest that even lower LDL levels should be achieved in order to protect high risk patients from premature CVD (1).

The establishment of a link between PCSK9 and cholesterol metabolism was rapidly followed by the discovery that selected mutations in the PCSK9 gene caused autosomal dominant hypercholesterolemia (2), suggesting that the mutations confer a gain-of-function (3) by increasing the normal activity of PCSK9. This was supported by the experiment in which wild-type and mutant PCSK9 (S127R and F216L) were expressed at high levels in the livers of mice; hepatic LDLR protein levels fell dramatically in mice receiving either the wild-type or mutant PCSK9 (4, 5). No associated reductions in LDLR mRNA levels were observed, indicating that overexpression of PCSK9, whether mutant or wild-type, reduces LDLRs through a post-transcriptional mechanism.

Given that gain-of-function mutations in PCSK9 cause hypercholesterolemia, it was reasonable to ask if loss-of-function mutations would have the opposite effect and result in hypocholesterolemia. Three loss-of-function mutations in PCSK9 (Y142X, L253F, and C679X) were identified in African-Americans (6). These mutations reduce LDL-C levels by 28% and were shown to decrease the frequency of CHD (defined as myocardial infarction, coronary death or coronary revascularization) by 88%. Rashid et al. (7) studied the mechanism of loss-of-function mutations in mice where PCSK9 was inactivated. They reported that these knockout mice showed increased hepatic LDLR protein (but not mRNA), increased clearance of circulating lipoproteins and reduced plasma cholesterol levels. Structure-function relationship analysis of the naturally occurring mutations in PCSK9 has also provided insights into the mechanism of action of PCSK9. Interestingly, mutations in PCSK9 that were found to be associated with the greatest reductions in LDL-C plasma levels are those that prevent the secretion of mature PCSK9 by disrupting its synthesis (Y142X), autocatalytic processing (L253F), or folding (C679X) (8). The Y142X mutation produces no detectable protein because it occurs early in the transcript and is predicted to initiate nonsense-mediated mRNA decay. Mutations in the catalytic domain (L253F) interfere with the autocatalytic cleavage of the protein. In cells expressing the PCSK9-253F, the amount of mature protein was reduced compared to that in cells expressing PCSK9-WT, suggesting that the mutation inhibits autocatalytic cleavage. The L253F mutation is near the catalytic triad (PCSK9 is a serine protease), therefore it might disrupt the active site (8). Inasmuch as autocatalytic cleavage of PCSK9 is required for export of the protein out of the ER, the L253F mutation delays transport of PCSK9 from the ER to the cell surface. The nonsense mutation (C679X) in PCSK9, which truncates the protein by 14 amino acids, did not interfere with protein processing, but the mature protein accumulates in the cells and none is secreted, suggesting that the protein is cleaved normally but is misfolded and is retained in the ER (8, 9).

The mechanism by which PCSK9 causes the degradation of the LDLR has not been fully elucidated. However, it is clear that the protease activity of PCSK9 is not required for LDLR degradation (10, 11). Li et al. (10) have co-expressed the prodomain and the catalytic domain in trans, and showed that the secreted PCSK9 was catalytically inactive, yet it is functionally equivalent to the wild-type protein in lowering cellular LDL uptake and LDLR levels. Similar studies were also reported by McNutt et al. (11). Furthermore, Zhang et al. (12) has mapped PCSK9 binding to the EGF-A repeat of the LDLR, and showed that such binding decreases the receptor recycling and increases its degradation. They also reported that binding to EGF-A domain was calcium-dependent and increased dramatically with reduction in pH from 7 to 5.2. Recently, Kwon et al. (13) determined the crystal structure of PCSK9 in complex with the LDLR-EGF-AB (EGF-A and EGF-B). The structure shows a well defined EGF-A domain, but the EGF-B domain is disordered and absent from their electron density map. The EGF-A domain binds to the PCSK9 catalytic domain at a site distant from the catalytic site, and makes no contact with either the C-terminal domain or the prodomain (14).

Several strategies have been proposed for targeting PCSK9 (15). Strategy 1: mRNA knockdown approaches include the use of antisense oligonucleotides or RNAi. Antisense oligonucleotides administered to mice reduced PCSK9 expression by >90% and lowered plasma cholesterol levels by 53% (16). A single intravenous injection of an RNAi delivered in lipidoid nanoparticles to cynomologous monkeys reduced plasma PCSK9 levels by 70% and plasma LDL-C levels by 56% (17). Strategy 2: is to prevent binding of PCSK9 to the LDLR on the cell surface with a small molecule, a peptide, or an antibody directed against PCSK9. Adding EGF-A fragments to cultured cells inhibits the ability of exogenously added PCSK9 to mediate LDLR degradation. Strategy 3: is to develop small-molecule inhibitors of the PCSK9 processing. Despite evidence that the catalytic activity of PCSK9 is not required for LDLR degradation (11), an intracellular inhibitor of PCSK9 catalytic activity should be effective, since autocatalytic processing of PCSK9 is required for secretion of the protein from the ER. Following its synthesis, PCSK9 undergoes an autocatalytic cleavage reaction that clips off the prodomain, but the prodomain remains attached to the catalytic domain (18, 19). The autocatalytic processing step is required for the secretion of PCSK9 (20), likely because the prodomain serves as a chaperone and facilitates folding. The continued attachment of the prodomain partially blocks the substrate binding pocket of PCSK9 (18, 19). McNutt et al. (21) demonstrated that antagonism of secreted PCSK9 increases LDLR expression in HepG2 cells. They show that an FH-associated LDLR allele (H306Y) that results in a gain-of-function mutation is due to an increase in the affinity of PCSK9 to the LDLR, which would lead to enhanced LDLR destruction, and decreased plasma LDL-C clearance. Furthermore, they were able to show elegantly that blocking the secreted PCSK9 with LDLR (H306Y) subfragment resulted in an increase in the level of LDLR in cultured HepG2 cells. Therefore, PCSK9 acts as a secreted factor to cause LDLR degradation, and a small molecule inhibitor that interferes with the autocatalytic process should decrease the amount of mature secreted PCSK9. This invention relates to identification of small molecules that down-regulate the function of PCSK9 using Strategy 2.

Recently (22-24), Regeneron/Sanofi and Amgen have reported Phase II proof-of-concept data that validate the blocking of PCSK9 with a monoclonal antibody as a strategy for lowering LDL-C in patients not controlled on standard statin therapy. They reported that a single injection of their drug, called REGN727, slashed LDL levels by more than 60% in clinical trial. Their approach follows Strategy 2 using antibodies instead of small molecules. This Strategy 2 is also being pursued by Merck, Novartis and Pfizer, while Strategy 1 is being pursued by Alnylam, Idera and Santaris (25).

SUMMARY OF THE INVENTION

This invention relates to therapeutic applications of small molecules that selectively interact with and down modulate PCSK9 function. In a first embodiment, the agents used in the practice of this invention have the general formula:

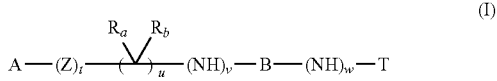

(I)

$$A-(Z)_t-\underset{u}{\overset{R_a\ R_b}{(\ \ )}}-(NH)_v-B-(NH)_w-T$$

wherein A is selected from the group consisting of:

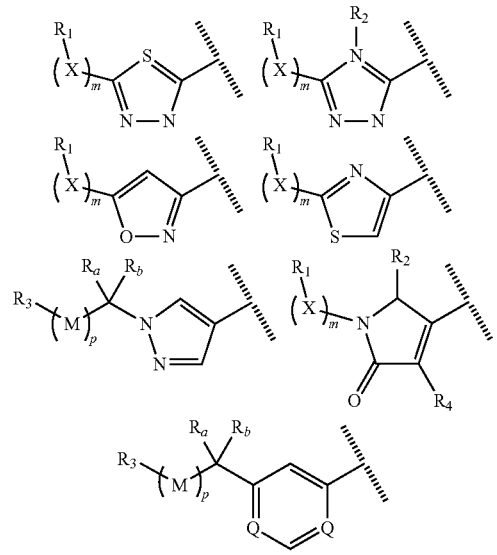

wherein $R^1$, $R^2$, and $R^3$ are independently selected from the group consisting of H and, optionally substituted, lower alkyl, alkenyl, alkynyl, cycloalkyl, aryl, heterocycle and heteroaryl; $R^4$ is selected from the group consisting of H, lower alkyl, OH, SH, $NH_2$, halo, CN, carboxyl, amido and carboxamido;

X is $(CH_2)_n$, O, S, $N(R^5)$ or a valence bond; $R^5$ is H or lower alkyl; and n is an integer from 1 to 3;

M is CONH, NHCO, $NHSO_2$, $NHCON(R^6)$ or a valence bond; $R^6$ is H or lower alkyl;

Q is independently CH or N;

Z is $CH_2$, S, O, or NH;

m and p are independently an integer from 0 to 1;

B is selected from the group consisting of C(=O) and $S(=O)_2$; T is selected from the group consisting of H, amino, alkoxy, carboxy, amido, aminocarbonyl, monoalkylaminocarbonyl, dialkylaminocarbonyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and, optionally substituted, lower alkyl, alkenyl, alkynyl, cycloalkyl, aryl, heterocycle, and heteroaryl;

$R_a$ and $R_b$ independently represent H or lower alkyl, and t, u, v and w are independently an integer from 0 to 1 with the proviso that at least one of v and w is 0;

and the pharmaceutically acceptable salts and all stereoisomers of the compound.

In one embodiment, the invention provides a method for the treatment or prophylaxis of hypercholesterolemia and/or at least one symptom of dyslipidemia, atherosclerosis, CVD or coronary heart disease in a patient in need of such treatment comprising administering to such a patient a therapeutically effective amount of a compound of formula I, above.

In another embodiment, the method of the invention involves administration of at least one compound of the following formula:

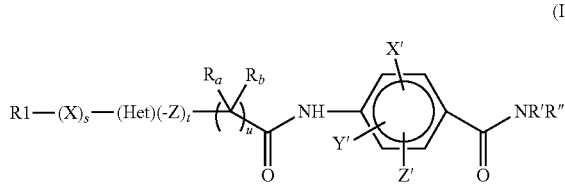

(II)

wherein Het is selected from the group of

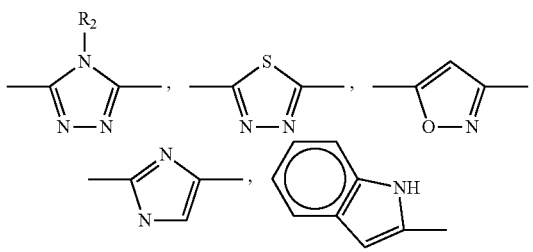

and $R_2$ is optionally substituted alkyl, cycloalkyl, aralkyl, aryl, heterocycle, heterocycloalkyl, heteroaryl, and heteroarylalkyl, X is selected from the group of $NR_c$, O, S, and a valence bond to $R_1$, and $R_c$ is H or lower alkyl;

Z is selected from the group of S, O, and $CH_2$;

$R^1$ is selected from the group of optionally substituted alkyl, cycloalkyl, aryl, aralkyl, heterocycle, heterocycloalkyl, heteroaryl, and heteroaralkyl;

$R_a$, $R_b$, R' and R" are independently selected from the group of H and lower alkyl;

$X^1$, $Y^1$ and $Z^1$ are the same or different and each represents hydrogen or a substituent from the group consisting of hydroxyl, halogen, amino, monoalkylamino, dialkylamino, alkoxy, carboxy, amido (including formamido, alkylamido and arylamido), aminocarbonyl, monoalkylaminocarbonyl, dialkylaminocarbonyl, carbamato, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and, optionally substituted, lower alkyl, alkenyl, alkynyl, cycloalkyl, aryl, heterocycle, and heteroaryl;

and s, t and u are independently an integer from 0 to 1;

In another embodiment, the invention provides compounds having the formula:

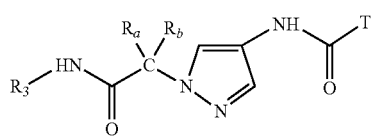

(III)

wherein T is selected from the group of optionally substituted alkyl, aralkyl, aryl, heterocycle, heterocycloalkyl, heteroaryl, and heteroarylalkyl; $R_3$ is selected from the group of optionally substituted alkyl, aralkyl, aryl, heterocyclylalkyl, heteroaryl, and heteroarylalkyl;

$R_a$ and $R_b$ are independently selected from the group of H and lower alkyl.

In another embodiment, the method of the invention involves the administration of at least one compound of the formula:

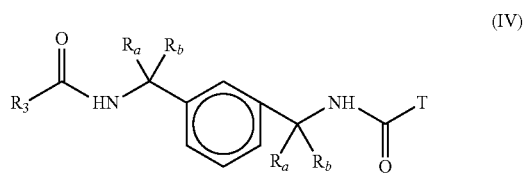

(IV)

wherein T and R3 are independently selected from the group of optionally substituted cycloalkyl, aryl, heterocycle, and heteroaryl;

and $R_a$ and $R_b$ are independently selected from the group of H and lower alkyl.

In another embodiment, the method of the invention involves administration of at least one compounds of the formula:

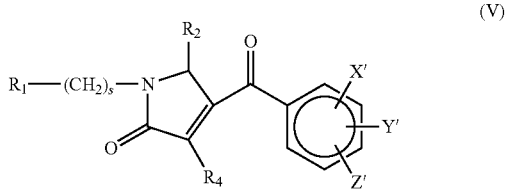

(V)

wherein $R_1$ is selected from the group of optionally substituted cycloalkyl, cycloalkyloxy, aryl, aryloxy, aralkoxy, heterocycle, heterocycloalkoxy, heteroaryl, and heteroaralkoxy;

$R_2$ is selected from the group of H and optionally substituted lower alkyl, cycloalkyl, aryl, heterocycle, and heteroaryl;

$R_4$ is selected from the group of H, lower alkyl, OH, SH, $NH_2$, halo, CN, carboxyl, and carboxamido;

wherein $X^1$, $Y^1$ and $Z^1$ are the same or different and each represents hydrogen or a substituent from the group consisting of hydroxyl, halogen, amino, monoalkylamino, dialkylamino, alkoxy, carboxy, amido (including formamido, alkylamido and arylamido), aminocarbonyl, monoalkylaminocarbonyl, dialkylaminocarbonyl, carbamato, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and, optionally substituted, lower alkyl, alkenyl, alkynyl, cycloalkyl, aryl, heterocycle, and heteroaryl;

and s is an integer from 1 to 4.

DESCRIPTION OF DRAWINGS AND TABLES

FIGS. 1A, B and C sets forth the structure of selected compounds that have an effect on LDLR upregulation as compared to control while having no effect on PCSK9 processing and secretion.

FIG. 2 shows the effect of different hits on PCSK9 synthesis, processing and secretion in HEK293 transfected cells. HEK-293T cells were seeded into 96 well plates in a DMEM containing 10% Fetal Bovine Serum media and incubated overnight at 37° C. Cells were transiently transfected with cDNA construct using the Lipofectamine-LTX. Compounds (25 uM) or vehicle were added, followed by additional 43 hours of incubation. Cellular PCSK9, secreted PCSK9, and cell viability were analyzed as described in Example 1 below.

FIG. 3 shows increased degradation of the LDLR by PCSK9. HEK-293T cells were seeded in a DMEM containing 10% Fetal Bovine Serum media and incubated overnight at 37° C. Cells were transiently transfected with Mock (lanes 1 and 2), PCSK9 (lanes 3 and 4), LDLR & PCSK9 (lanes 5 and 6), and LDLR (lanes 7 and 8) cDNA constructs using the Lipofectamine-LTX. Cells were incubated for an additional 72 hrs, and cells and media were analyzed as in text.

FIG. 4 shows upregulation of LDLR by PCSK9 antagonists. HEK-293T cells were seeded in a DMEM containing 10% Fetal Bovine Serum media and incubated overnight at 37° C. Cells were transiently transfected with LDLR & PCSK9 cDNA constructs using the Lipofectamine-LTX as described above. After 24 hrs, cells were treated with different compounds and incubated for an additional 48 hrs. Cells were assayed as described above for LDLR expression.

FIG. 5 shows effect of different hits on LDLR upregulation in HepG2 cells. HepG2 cells were seeded into 96 well plates in a MEM containing 10% Fetal Bovine Serum media and incubated overnight at 37° C. Cells were transiently transfected with PCSK9 cDNA constructs using the Lipofectamine-LTX. Compounds were added, followed by additional 43 hours of incubation. The cells were lysed and analyzed for LDLR expression and cell viability determined as described above.

FIG. 6 shows increased uptake of Fluorescent Dil-LDL using various concentrations of two inhibitors in HepG2 cells. The SBC compounds were validated for their ability to increase uptake of Fluorescent Dil-LDL in HepG2 cells. The data show that an increase in the Fluorescent Dil-LDL uptake using submicromolar concentrations of SBC-115, 076.

FIG. 7 shows the different treatments for each of the five groups of animals used to test the efficacy of SBC-115,076 and Atorvastatin.

FIG. 8 shows the effect of SBC-115,076 and atorvastatin on serum total cholesterol levels of 8 mice fed high fat diet (HFD) compared to animals fed regular diet.

DETAILED DESCRIPTION OF THE INVENTION

Figure 1A:
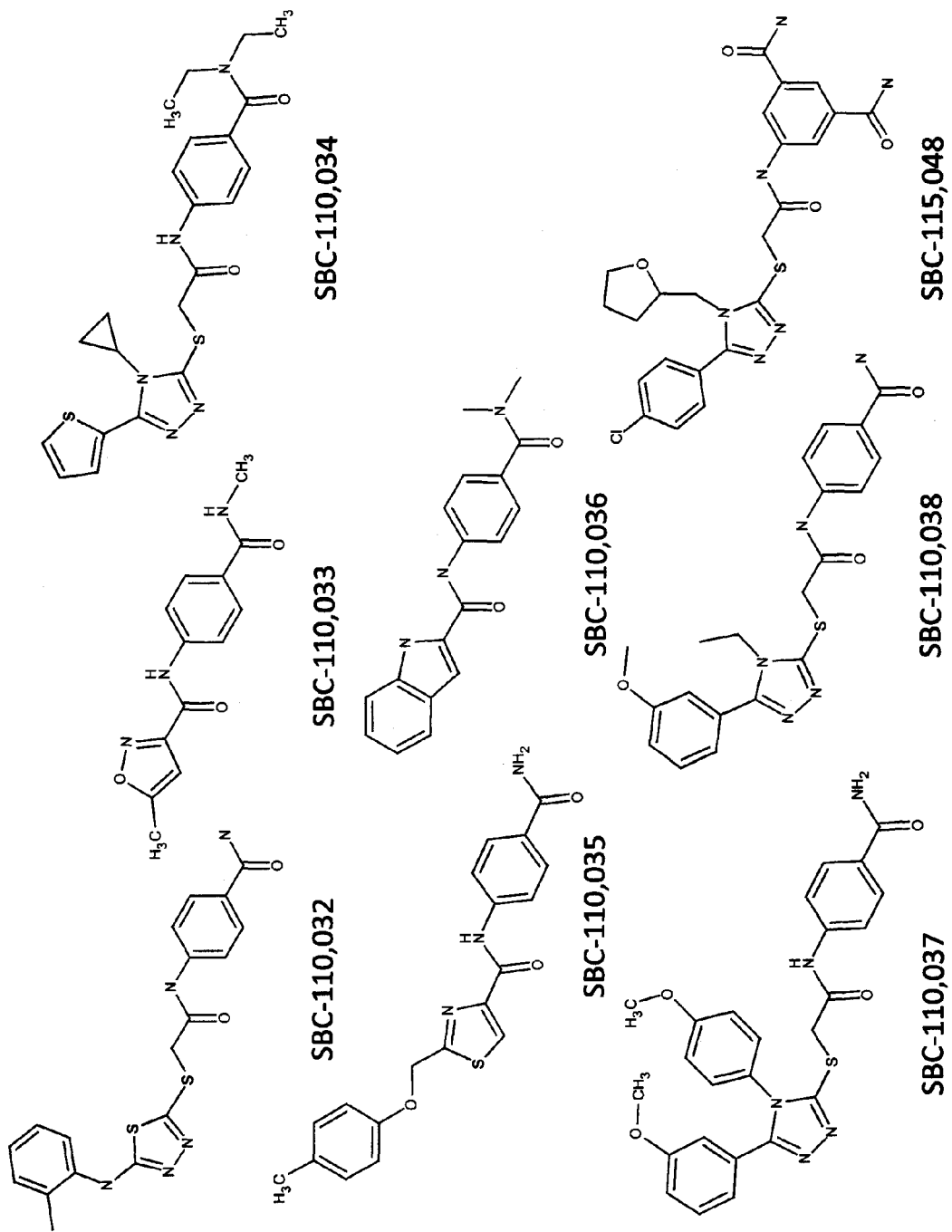

The present invention relates to small molecules that down regulate the function of extracellular proprotein convertase subtilisin kexin type 9 (PCSK9), including its interaction with the low density lipoprotein (LDL) receptor (LDLR), and methods of using these antagonists as a medicament. The small molecule modulators of PCSK9 function can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

As used herein, the term "lower alkyl" denotes branched or unbranched hydrocarbon chains, having 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxy, halogen, mercapto or thio, cyano, alkylthio, carboxy, carbalkoxy, amino, nitro, alkoxy, or optionally substituted, alkenyl, alkynyl, heterocyclyl, aryl, heteroaryl, and the like to form alkyl groups such as trifluoro methyl, 3-hydroxyhexyl, 2-carboxypropyl, 2-fluoroethyl, carboxymethyl, cyanobutyl, phenethyl, benzyl and the like.

The term "halogen" or "halo" as used herein alone or as part of another group refers to chlorine, bromine, fluorine, and iodine.

The term "alkoxy" refers to alkyl-O—, in which alkyl is as defined above.

The term "alkylthio" refers to alkyl-S—, in which alkyl is as defined above.

The terms "amino", "monoalkylamino", "dialkylamino" refer to the moiety —NR'R", in which R' and R", each independently represents H, alkyl or aryl, all as defined herein.

The term "carboxy" refers to the moiety —C(=O)OH.

The term "carbalkoxy" refers to the moiety —C(=O)O-alkyl, in which alkyl is as defined above.

The term "amino (monoalkylamino-, dialkylamino-) carbonylamino" refers to the moiety —NHC(=O)NR'R", in which R'R", each independently represents H, alkyl or aryl, all as defined herein.

The term "carbamato" refers to the moiety —NR'C(=O)OR", in which R' and R", each independently represents H, alkyl or aryl, all as defined herein.

The term "amino (monoalkylamino, dialkylamino) carbonyl" (also "carboxamido") refers to the moiety —C(=O)NR'R", in which R' and R" each independently represents H, alkyl, or aryl, all as defined herein.

The term "amido" refers to the moiety —NRC(=O)—R", in which R' and R", each independently represents H, alkyl or aryl, all as defined herein.

The term "alkylsulfonyl" refers to the moiety —S(=O)2-alkyl, in which alkyl is as previously defined.

The term "alkylsulfonyloxy" refers to the moiety —OS(=O)2-alkyl, wherein alkyl is as previously defined.

The term "amino (monoalkylamino-, dialkylamino-) sulfinyl" refers to the moiety —S(=O)NR'R" in which R' and R" each independently represents H, alkyl or aryl, all as defined herein.

The term "amino (monoalkylamino-, dialkylamino-) sulfonyl" refers to the moiety —S(=O)2NR'R", in which R' and R" each independently represents H, alkyl or aryl, all as defined herein.

The term "alkylsulfonylamino" refers to the moiety —NHS(=O)2-alkyl, in which alkyl is as previously defined.

The term "hydroxysulfonyloxy" refers to the moiety —OS(=O)2OH.

The term "alkoxysulfonyloxy" refers to the moiety —OS(=O)2O-alkyl, in which alkyl is as previously defined.

The term "alkylsulfonyloxy" refers to the moiety —OS(=O)2-alkyl, in which alkyl is as previously defined.

The term "hydroxysulfonyl" refers to the moiety —S(=O)2OH.

The term "alkoxysulfonyl" refers to the moiety —S(=O)2O-alkyl, wherein alkyl is as previously defined.

The term "alkylsulfonylalkyl" refers to the moiety -alkyl-S(=O)2-alkyl, wherein alkyl (each instance) is as previously defined.

The term "amino (monoalkylamino-, dialkylamino-) sulfonylalkyl" refers to the moiety -alkyl-S(=O)2-NR'R", wherein alkyl is as previously defined, and R' and R" each independently represents H, alkyl or aryl, all as defined herein.

The term "amino (monoalkylamino-, dialkylamino-) sulfinylalkyl" refer to the moiety -alkyl-S(=O)—NR'R", wherein alkyl is as previously defined, and R' and R" each independently represents H, alkyl or aryl, all as defined herein.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl cyclododecyl and cyclohexenyl, "Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl or cycloheteroalkyl rings or substituted forms thereof.

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonyl, monoalkylaminocarbonyl, dialkylaminocarbonyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents mentioned in the definitions), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" or "Het" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" "substituted cycloalkyl" and "substituted aryl". Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

The term "heterocyclo", "heterocycle" or "heterocyclic ring," as used herein alone or as part of another group, represents an unsubstituted or substituted stable 5- to 7-membered monocyclic ring system which may be saturated or partially unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. "Substituted heterocyclo (or heterocycle or heterocyclic ring) includes a heterocyclic group optionally substituted with 1 to 4 substituents, such as the substituents included above in the definition of "substituted alkyl" "substituted cycloalkyl" and "substituted aryl". The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The term "optionally substituted" is used herein to signify that a chemical moiety referred to, e.g., alkyl, aryl, heteroaryl, may be unsubstituted or substituted with one or more groups including, without limitation, lower alkyl, alkenyl, alkynyl, cycloalkyl, arylalkyl, aryl, haloaryl, heterocycle, heterocycloalkyl, heteroaryl, hydroxyl, amino, monoalkylamino, dialkylamino, alkoxy, halogen, haloalkoxy, aryloxy, aryloxyalkyl, alkylaryloxy, arylalkoxy, alkoxyaryl, carboxy, carbalkoxy, carboxamido, aminocarbonyl, monoalkylaminocarbonyl, dialkylaminocarbonyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of formulas I-V, above, that may be optionally substituted include lower alkyl, alkenyl, alkynyl, cycloalkyl, arylalkyl, aryl, heterocycle, and heteroaryl. For example, optionally substituted alkyl would comprise both propyl and 2-chloro-propyl. Additionally, "optionally substituted" is also inclusive of embodiments where the named substituent or substituents have multiple substituents rather than simply a single substituent. For example, optionally substituted aryl would comprise both phenyl and 3-bromo-4-chloro-6-ethyl-phenyl.

As used herein, the term "subject" includes both humans and animals. As used herein, the term "PCSK9" refers to any form of the protein PCSK9, including PCSK9 mutants and variants, which retain at least part of PCSK9 activity or function. Unless otherwise indicated, such as by specific reference to human PCSK9, PCSK9 refers to all mammalian species of native sequence PCSK9, e.g., human, porcine, bovine, equine, canine and feline. One exemplary human PCSK9 sequence is found as Uniprot Accession Number Q8NBP7 (SEQ ID NO:16).

As used herein, a "modulator of PCSK9 function" refers to a small molecule that is able to inhibit PCSK9 biological activity or function, and/or downstream pathway(s) mediated by PCSK9 signaling, including PCSK9-mediated down-regulation of the LDLR, and PCSK9-mediated inhibition of the decrease in LDL blood clearance. A modulator of PCSK9 function encompasses compounds that block, antagonize, suppress or reduce (to any degree including significantly) PCSK9 biological activity, including downstream pathways mediated by PCSK9 signaling, such as LDLR interaction and/or elicitation of a cellular response to PCSK9. For purpose of the present invention, it will be explicitly understood that the term "modulator of PCSK9 function" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and inhibit the decrease in blood LDL clearance), or the consequences of the biological activity, are substantially nullified, decreased, or neutralized in any measurable degree. In some embodiments, a modulator of PCSK9 function binds PCSK9 and prevents its interaction with the LDLR or its secretion. In other embodiments, a modulator of PCSK9 function binds to the active site of PCSK9 to stabilize its zymogen and prevent autoprocessing. In further embodiments, a modulator of PCSK9 function decreases or blocks PCSK9 mediated down-regulation of the LDLR; inhibits the PCSK9-mediated decrease in LDL blood clearance; increases LDL clearance in media by cultured hepatocytes; increases blood LDL clearance by the liver in vivo; improves patients' sensitivity to other LDL lowering drugs, including statins; is synergistic to other LDL lowering drugs, including statins; and blocks PCSK9 interaction with other yet to be identified factors. Examples of modulators of PCSK9 function are provided herein.

The compounds used in the method of the invention can be administered as salts, which are also within the scope of this invention. Pharmaceutically acceptable (i.e., non-toxic, physiologically compatible) salts are preferred. If the compounds of the method of the present invention have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid or lysine or arginine, or benzoic acid, or with organic sulfonic acids, such as (C1-C4) alkyl or arylsulfonic acids which are unsubstituted or substituted, for example by halogen, for example methyl- or para-toluene-sulfonic acid. Corresponding acid addition salts can also be formed having plural basic centers, if desired. The compounds used in the method of the present invention having at least one acid group (for example COOH) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may also be formed.

Preferred salts of the compounds described herein which contain a basic group include monohydrochloride, hydrogensulfate, methanesulfonate, phosphate or nitrate.

Preferred salts of the compounds described herein which contain an acid group include sodium, potassium and magnesium salts and pharmaceutically acceptable organic amines.

All stereoisomers of the compounds which may be used in the methods described herein, either in a mixture or in pure or substantially pure form, are considered to be within the scope of this invention. The compounds of the present invention can have asymmetric centers at any of the carbon atoms including any one of the R substituents. Consequently, compounds used in the method of the invention can exist in enantiomeric or diastereomeric forms or in mixtures thereof. The processes for preparation of such compounds can utilize racemates, enantiomers or diastereomers as starting materials. When diastereomeric or enantiomeric products are prepared, they can be separated by conventional methods for example, chromatographic, chiral HPLC or fractional crystallization.

As used herein, the term "pharmacophore" refers to the ensemble of steric and electronic features that are necessary to ensure the optimal supramolecular interactions with a specific biological target structure and to trigger, activate, block, inhibit or modulate the biological target's biological activity, as the case may be. See, IUPAC, *Pure and Applied Chemistry* (1998) 70: 1129-1143.

As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water molecule. An ordered water molecule is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds, ionic bonds, and hydrophobic interactions. A pharmacophore model can be derived from two or more bound conformations of a ligand.

As used herein, the term "ligand" refers to any compound, composition or molecule that interacts with the ligand binding domain of a receptor and modulates its activity. A "ligand" may also include compounds that modulate the receptor without binding directly to it.

In carrying out the method of the invention, the above-described compounds may be administered as such, or in a form from which the active agent can be derived, such as a prodrug. A prodrug is a derivative of a compound described herein, the pharmacologic action of which results from the conversion by chemical or metabolic processes in vivo to the active compound. The term "prodrug esters" as employed herein includes esters and carbonates formed by reacting one or more hydroxyls of compounds used in the method of the invention with alkyl, alkoxy, or aryl substituted acylating agents employing procedures known to those skilled in the art to generate acetates, pivalates, methylcarbonates, benzoates and the like. Any compound that can be converted in vivo to provide the bioactive agent (i.e., a compound of formula I) is a prodrug within the scope and spirit of the invention. Various forms of prodrugs are well known in the art. A comprehensive description of prodrugs and prodrug derivatives are described in: (a) The Practice of Medicinal Chemistry, Camille G. Wermuth et al., Ch 31 (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., Ch. 5, pgs, 113-191 (Harwood Academic Publishers, 1991).

The therapeutic agent used in practicing the method of the invention is administered in an amount sufficient to induce the desired therapeutic effect in the recipient thereof. Thus the term "therapeutically effective amount" as used herein refers to an amount of a therapeutic agent which is sufficient to treat or prevent a condition treatable by administration of one or more of the compounds of formulas I-V or a prodrug thereof. Preferably, the therapeutically effective amount refers to the amount appropriate to treat a PCSK9-associated condition, i.e. to bring almost a detectable therapeutic or preventative or ameliorative effect. The effect may include, for example, treatment or prevention of the conditions described herein.

The compound(s) described herein may be administered at a dose in range from about 0.01 mg to about 200 mg/kg of body weight per day. A dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in the method of the invention will typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist.

In one aspect, the invention provides a method for treating or preventing hypercholesterolemia, and/or at least one symptom of dyslipidemia, atherosclerosis, CVD or coronary heart disease, in an individual comprising administering to the individual an effective amount of a modulator of PCSK9 function that antagonizes circulating PCSK9.

In a further aspect, the invention provides an effective amount of a modulator of PCSK9 function that antagonizes circulating PCSK9 for use in treating or preventing hypercholesterolemia, and/or at least one symptom of dyslipidemia, atherosclerosis, CVD or coronary heart disease, in an individual. The invention further provides the use of an effective amount of a modulator of PCSK9 function that antagonizes extracellular or circulating PCSK9 in the manufacture of a medicament for treating or preventing hypercholesterolemia, and/or at least one symptom of dyslipidemia, atherosclerosis, CVD or coronary heart disease, in an individual.

The methods of the invention use a modulator of PCSK9 function, which refers to any molecule that blocks, suppresses or reduces (including significantly reduces) PCSK9 biological activity, including downstream pathways mediated by PCSK9 signaling, such as elicitation of a cellular response to PCSK9.

A modulator of PCSK9 function should exhibit any one or more of the following characteristics: (a) bind to PCSK9; (b) decrease or block PCSK9 interaction with the LDLR; (c) decrease or block secretion of PCSK9; (d) decrease or block PCSK9 mediated down-regulation of the LDLR; (e) inhibit the PCSK9-mediated decrease in LDL blood clearance, (f) increase LDL clearance in media by cultured hepatocytes, (g) increase blood LDL clearance by the liver in vivo, (h) improve patients' sensitivity to other LDL lowering drugs, including statins, (i) is synergistic to other LDL lowering drugs, including statins; and (j) block PCSK9 interaction with other yet to be identified factors.

In general, the compound(s) used in the method of the invention can be administered to achieve modulation of PCSK9 function by using any acceptable route known in the art, either alone or in combination with one or more other therapeutic agents. Thus, the active agent(s) can be administered orally, buccally, parenterally, such as by intravenous or intra-arterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

As used herein, the expression "physiologically compatible carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, $20^{th}$ edition (A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. Except insofar as any conventional pharmaceutical carrier medium is incompatible with the PCSK9 modulators used in the present invention, such as by producing an undesirable biological effect or otherwise interacting in an deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of the active agent, which involves incorporation of the active agent into a suitable delivery system. This dosage form controls release of the active agent(s) in such a manner that an effective concentration of the active agent(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

In pharmaceutical compositions used in practicing the method of the invention, the active agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

Figure 1B:
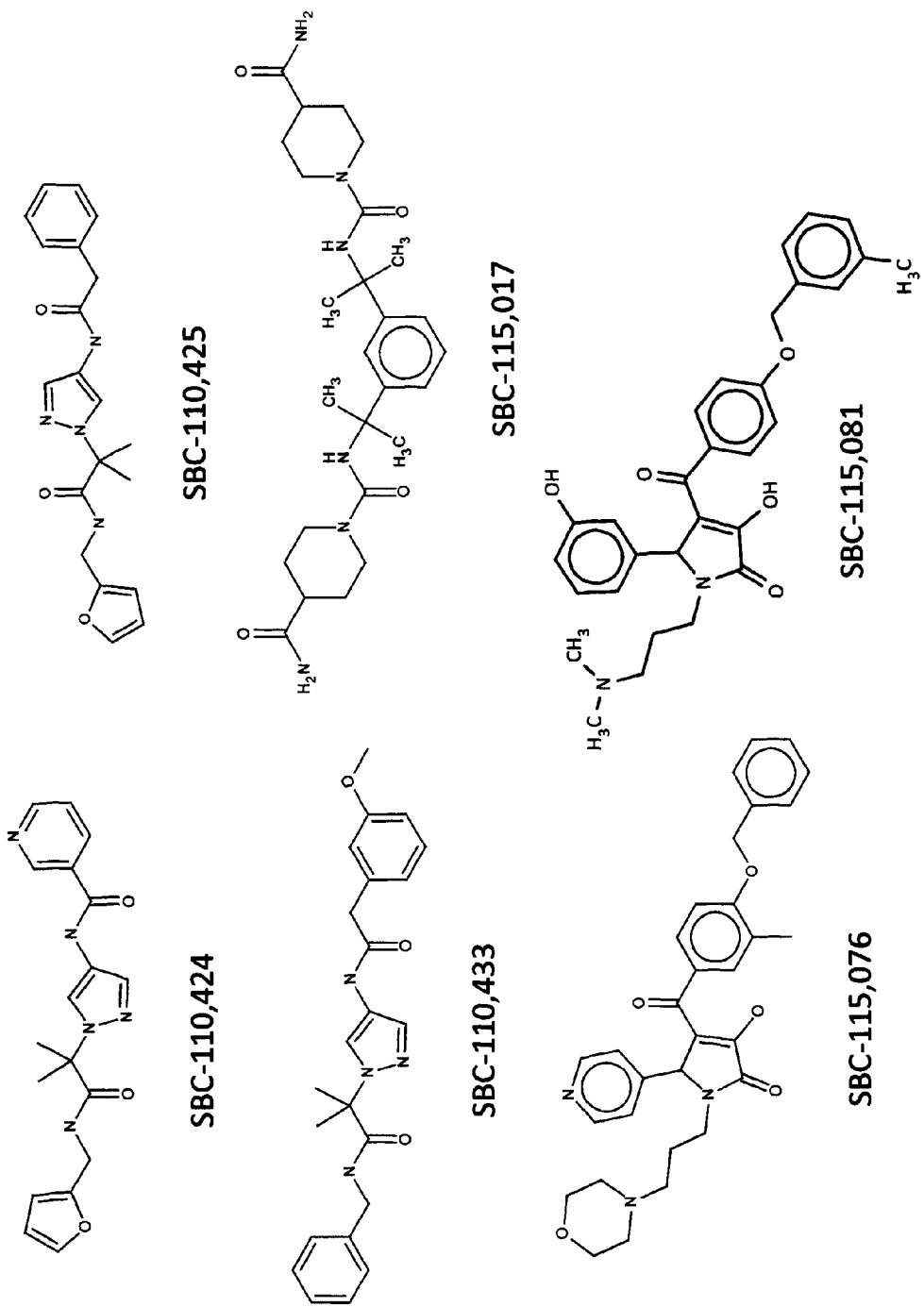
Figure 1C:
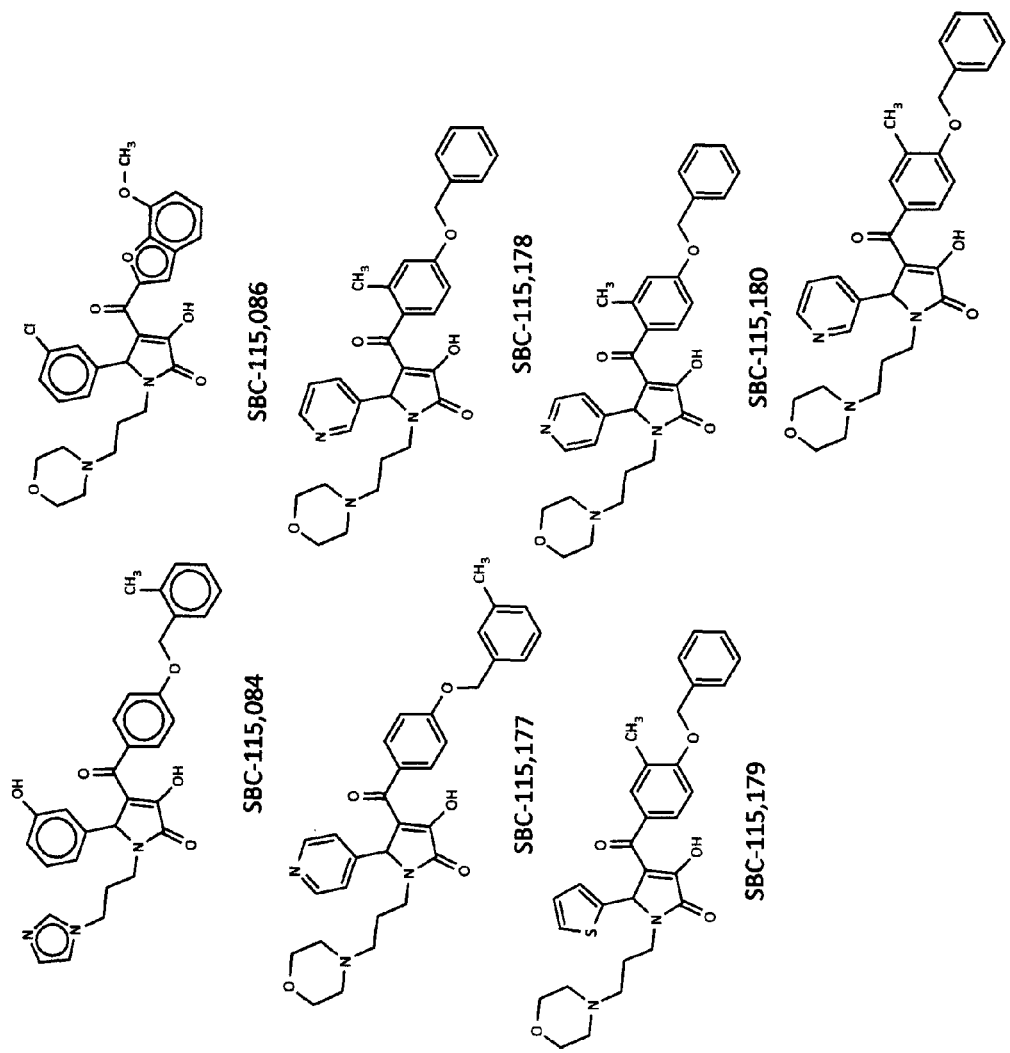

Preferred compounds for use in practicing this invention include those of formulas II-V, above. More preferred are the compounds set out in FIG. 1.

The compounds described herein are obtainable from commercial sources, such as BioFocus/Galapagos (SBC-110,424, 110,425 and 110,433), Enamine (SBC-110,032 through 038), and Ambinter (SBC-115,017, 115,048 and 115,076, 115,081, 115,084, 115,086, and 115,177 through 181).

The methods of the present invention will normally include medical follow-up to determine the therapeutic or prophylactic effect brought about in the subject undergoing treatment with the compound(s) and/or composition(s) described herein.

The activities of compounds described herein have been experimentally demonstrated. The following examples are provided to describe the invention in further detail. These examples are provided for illustrative purposes only and are not intended to limit the invention in any way.

Example 1

Test for Secreted PCSK9

Figure 2:
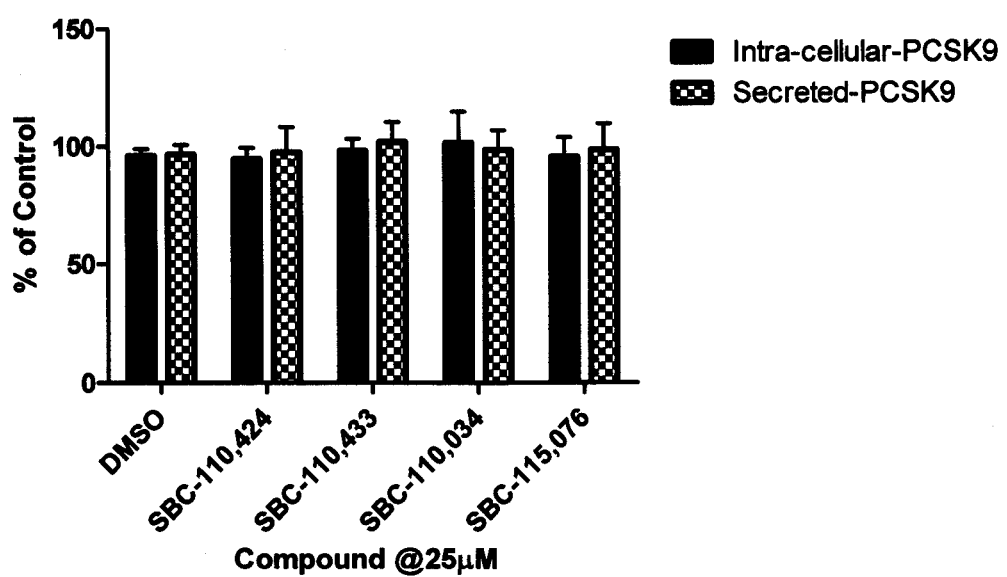

HEK-293T cells were seeded into 96-well plates in a DMEM containing 10% Fetal Bovine Serum media and incubated overnight at 37° C. Cells were transiently transfected with cDNA construct using the Lipofectamine-LTX. Compounds (25 uM) or vehicle were added, followed by additional 43 hours of incubation. Cellular PCSK9, secreted PCSK9, and cell viability were analyzed for PCSK9 secretion using western blot analysis, imaged and quantitated using a LAS-4000 (GE). Results from selected compounds are shown in FIG. 2.

Example 2

Test for LDLR Upregulation

Figure 3:
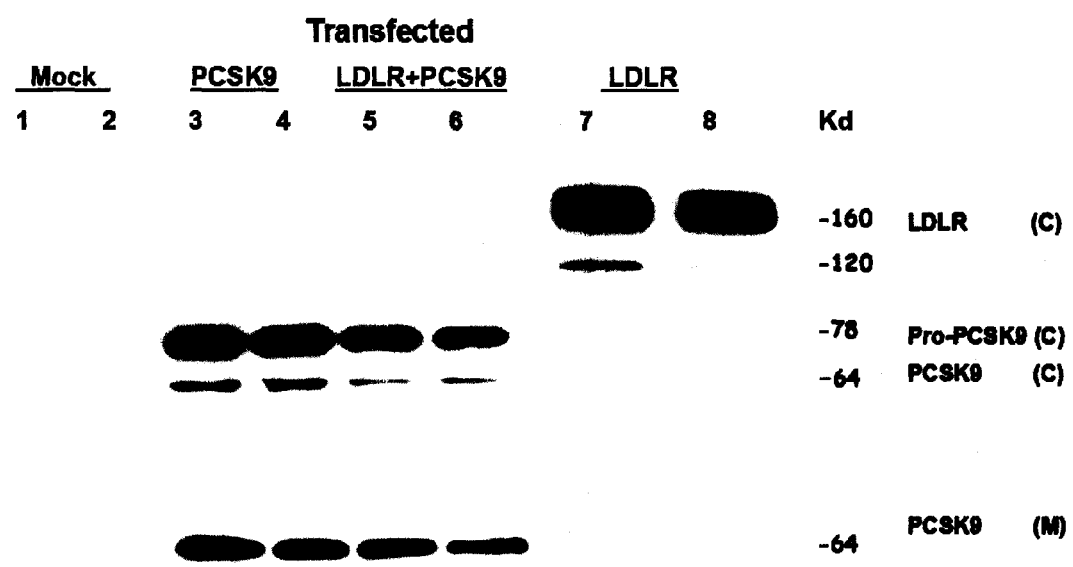
Figure 4:
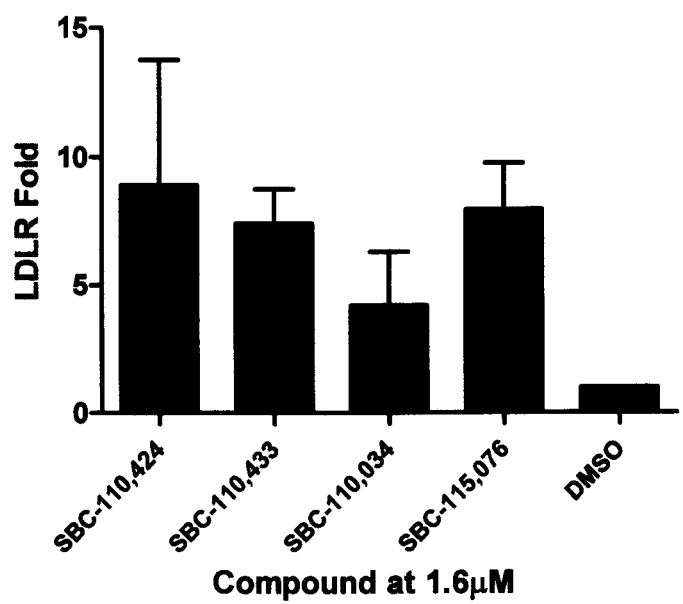

We used our own recombinant assay which demonstrates that co-expression of PCSK9 and LDLR DNA in HEK-293 cells results in a decrease in the expression level of intracellular LDLRs. We have constructed the expression vector of human LDLR under the control of the cytomegalovirus promoter-enhancer (pCMV-LDLR). In addition, a construct containing the PCSK9 (pCMV-PCSK9-FLAG) was described above. These constructs were used to transiently transfect mammalian cells and both cell lysate and supernatant were subjected to SDS-PAGE and immunoblot analysis using an anti-PCSK9 or LDLR antibody. The data from the blot showed that cells that were transfected with only pCMV-PCSK9-FLAG expressed both the unprocessed (cells) and processed (media) PCSK9 (FIG. 3). Cells that were transfected with only pCMV-LDLR showed expression of the LDLR in the cells (FIG. 3). However, cells that were transfected with both pCMV-PCSK9-FLAG and pCMV-LDLR showed disappearance of the intracellular LDLR band (FIG. 3), which provides further evidence that the presence of PCSK9 results in degradation of LDLR or chaperones it to the degradation pathway. Addition of inhibitors of PCSK9 processing to the latter cells should result in decreased degradation of the LDLR and the appearance of the 160K Dalton band on the gel. Using this assay, we tested our compounds for their ability to reduce the degradation of the LDLR. HEK-293 cells were used in this assay. They were grown in 96-well plates overnight, and transfected with LDLR/PCSK9. Compounds dissolved in DMSO or vehicle were added to the culture media, and incubated for 24-48 hours; cells were lysed. Cell lysates were subjected to quantitation using the above immunoassay (FIG. 4).

Figure 5:
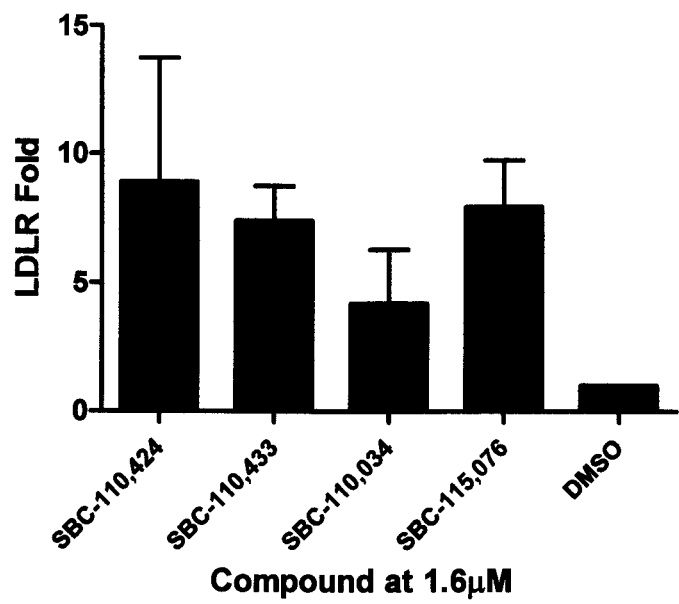

Testing confirmed that these compounds are capable of up regulating the endogenously expressed LDLR in HepG2 cells. HepG2 transfected with PCSK9 cells were cultured in 96-well plates at a density of 30,000 cells per well. The next day, cells are treated with selected screening compounds or vehicle. Cells were incubated for 48 hrs and then subjected to quantitation using an LDL receptor-polyclonal antibody and analyzed as described above. The data in FIG. 5 shows that these compounds exhibited an increase in the level of LDLR as compared to cells treated with same volume of DMSO with several fold upregulation of LDLR Example 3

Uptake of Dil-LDL in HepG2 Cells In Situ

Figure 6:
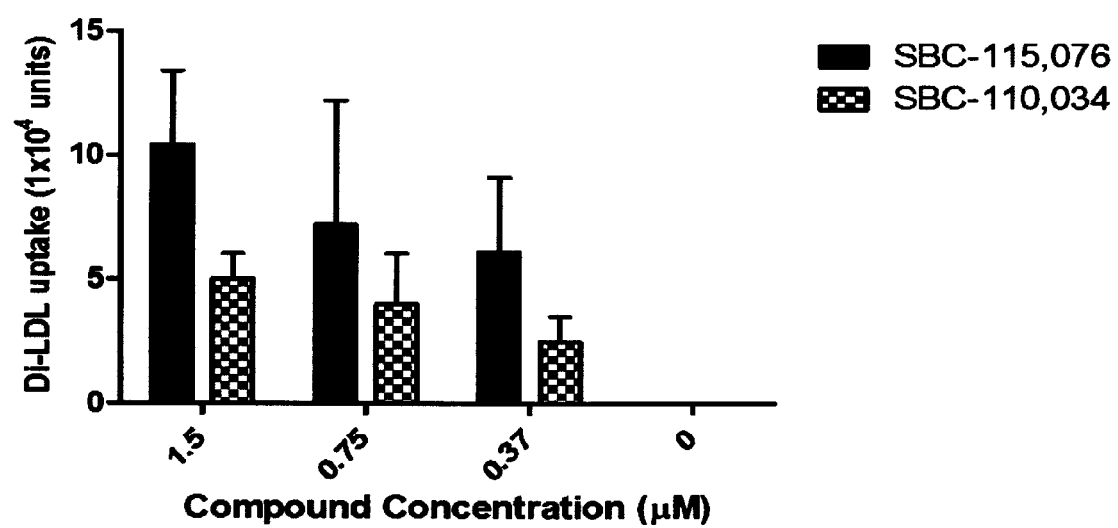

We also tested the ability of the PCSK9 compounds to enhance the uptake of Fluorescent Dil-LDL in HepG2 cells. Briefly, HepG2 cells were plated and allowed to grow overnight. Compounds were added to the cells followed by the addition of Fluorescent Dil-LDL. Cells were washed extensively, and the Fluorescent Di-LDL taken up by the cells were measured using the Synergy 2 plate reader (FIG. 6).

Example 4

Test for Cell Viability

All compounds that inhibit PCSK9 secretion were used to test for in situ cell viability. HEK-293T cells or HepG2 cells were seeded in 96-well plates in a cell media containing 10% Fetal Bovine Serum and incubated overnight at 37° C. Compounds at various concentrations were added to cells after 24 hours and incubated for an additional 48 hours. Cell viability was assayed using Resazurin (Sigma 199303) and an Envision 2101 Multi-label plate reader.

The foregoing specification includes citations to certain publications, which are provided to indicate the state of the art to which this invention pertains. The entire disclosure of each of the cited publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All compositions and methods of use thereof that embody the present invention can, in alternate embodiments, be more specifically defined by any of the transitional terms "comprising," "consisting essentially of," and "consisting of."

Example 5

Test for Efficacy in Animal Model

SBC-115,076, and SBC-110,034 were tested for their efficacy in male mice (C57BL/6 mice). Mice were housed as four animals per cage under climate-controlled conditions of temperature (20-24° C.), humidity (60-70%), and alternating 12 h light/dark cycles. The mice were divided into five groups as shown in FIG. 7. One group was fed commercial chow diet (Prolab RMH 3000, PMI feeds, St. Louis, Mo.) to serve as a negative control, while the other four groups were fed high fat diet (TD.06414), which provides 60% of calories from fat. Water was provided ad libitum. Plasma was collected once weekly to monitor the level of LDL. After 4 weeks of feeding a high fat-diet, mice were randomly assigned to one of several groups such that the average LDL levels were equal among different groups. One of the four groups of mice fed high fat diet was treated with vehicle and served as a positive control, whereas each of the other three groups was treated daily with 8 mg/kg of one of the above-mentioned compounds subcutaneously for two weeks. Blood samples (75 µl) were collected twice weekly after drug administration from the retro-orbital venous plexus via heparinized capillary tubes containing 2 USP units of ammonium heparin per tube (Carolina, Burlington, N.C.). Plasma were separated immediately by centrifugation (5,000×g) for 5 min at room temperature and then kept at −80° C. until assayed for lipid profile. Plasma cholesterol, LDL-C, HDL-C, and triglyceride levels are measured enzymatically. Additionally, the plasma levels of PCSK9 and chemokines/cytokines were measured for potential pleiotropic effects of PCSK9 inhibitors using ELISA and multiplex assays.

The data obtained demonstrated that SBC-115,076 and SBC-110,034 lowered cholesterol levels in mice that are fed high fat diet. FIG. 8 shows data obtained with SBC-115,076 indicating a mean of 32% reduction ($P<0.01$) in total cholesterol levels after two weeks relative to high fat diet animal levels and a mean 50% reduction ($P<0.01$) toward return to regular diet cholesterol levels.

Figure 9:
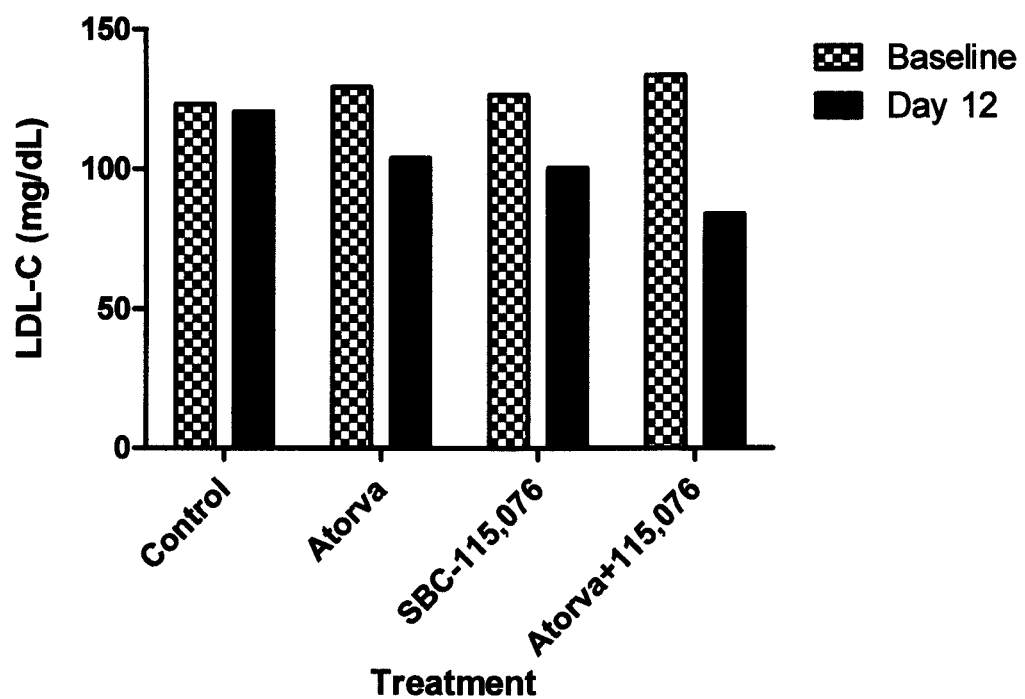
FIG. 9 shows the effect of combinations of SBC-115,076 and atorvastatin on plasma LDL-C in mice fed High Fat Diet.

A second study was conducted with Atorvastatin (40 mg/kg, for 3 weeks). The data demonstrated that with Atorvastatin a mean of 27% reduction ($P<0.01$) in total cholesterol levels after three weeks relative to high fat diet animal levels and a mean 44% reduction ($P<0.01$) toward return to regular diet cholesterol levels (FIG. 9).

REFERENCES

1. Grundy S M, Cleeman J I, Merz C N B, Brewer, Jr, H B, Clark L T, Hunninghake D B, Pasternak R C, Smith, Jr, S C, Stone N J (2004). Implications of Recent Clinical Trials for the National Cholesterol Education Program Adult Treatment Panel III Guidelines. *Circulation* 110, 227-239.

2. Abifadel M, Varret M, Rabès J, Allard D, Ouguerram K, Devillers M, Cruaud C, Benjannet S, Wickham L, Erlich D, Derré A, Villéger L, Farnier M, Beucler I, Bruckert E, Chambaz J, Chanu B, Lecerf J, Luc G, Moulin P, Weissenbach J, Prat A, Krempf M, Junien C, Seidah N, Boileau C (2003). Mutations in PCSK9 cause autosomal dominant hypercholesterolemia. *Nat. Genet* 34, 154-156.
3. Pisciotta L, Priore Oliva C, Cefalu A B, Noto D, Bellocchio A, Fresa R, Cantafora A, Patel D, Avema M, Tarugi P, Calandra S, Bertolini S (2006). Additive effect of mutations in LDLR and PCSK9 genes on the phenotype of familial hypercholesterolemia. *Atherosclerosis* 186, 433-440.
4. Maxwell K, Breslow J (2004). Adenoviral-mediated expression of PCSK9 in mice results in a low-density lipoprotein receptor knockout phenotype. *Proc Natl Acad Sci USA* 101, 7100-7105.
5. Benjannet S, Rhainds D, Essalmani R, Mayne J, Wickham L, Jin W, Asselin M, Hamelin J, Varret M, Allard D, Trillard M, Abifadel M, Tebon A, Attie A D, Rader D J, Boileau C, Brissette L, Chrétien M, Prat A, Seidah N G (2004). NARC-1/PCSK9 and its natural mutants: zymogen cleavage and effects on the low density lipoprotein (LDL) receptor and LDL cholesterol. *J Biol Chem* 279, 48865-48875.
6. Cohen J, Pertsemlidis A, Kotowski I, Graham R, Garcia C, Hobbs H (2005). Low LDL cholesterol in individuals of African descent resulting from frequent nonsense mutations in PCSK9. *Nature Genetics* 37, 161-165.
7. Rashid S, Curtis D, Garuti R, Anderson N, Bashmakov Y, Ho Y, Hammer H, Moon Y, Horton J (2005). Decreased plasma cholesterol and hypersensitivity to statins in mice lacking PCSK9. *Proc Natl Acad Sci USA* 102, 5374-5379.
8. Zhao Z, Tuakli-Wosornu Y, Lagace T, Kinch L, Grishin N, Horton J, Cohen J, Hobbs H (2006). Molecular Characterization of Loss-of-Function Mutations in PCSK9 and Identification of a Compound Heterozygote. *Am J Human Genetics* 79, 514-523.
9. Benjannet S, Rhainds D, Hamelin J, Nassoury N, Seidah N G (2006). The proprotein convertase PCSK9 is inactivated by furin and/or PC5/6A: functional consequences of natural mutations and post-translational modifications. *J Biol Chem* 281, 30561-30572.
10. Li J, Tumanut C, Gavigan J-A, Huang W-J, Hampton E N, Tumanut R, Suen K F, Trauger J W, Spraggon G, Lesley S A, Liau G, Yowe D, Harris J L (2007). Secreted PCSK9 promotes LDL receptor degradation independently of proteolytic activity. *Biochem J* 406, 203-207.
11. McNutt M C, Lagace T A, Horton J D (2007). Catalytic activity is not required for secreted PCSK9 to reduce low density lipoprotein receptors in HepG2 cells. *J Biol Chem* 282, 20799-20803.
12. Zhang D-W, Lagace T A, Garuti R, Zhao Z, McDonald M, Horton J D, Cohen J C, Hobbs H H (2007). Binding of proprotein convertase subtilisin/kexin type 9 to epidermal growth factor-like repeat A of low density lipoprotein receptor decreases receptor recycling and increases degradation. *J Biol Chem* 282, 18602-18612.
13. Kwon H J, Lagace T A, McNutt M C, Jay D. Horton J D, Deisenhofer J (2008). Molecular basis for LDL receptor recognition by PCSK9. *Proc Natl Acad Sci USA* 105, 1820-5.
14. Bottomley M J, Cirillo A, Orsatti L, Ruggeri L, Fisher T S, Santoro J C, Cummings R T, Cubbon R M, Lo Surdo P, Calzetta A, Noto A, Baysarowich J, Mattu M, Talamo F, De Francesco R, Sparrow C P, Sitlani A, Carfi A (2009). Structural and biochemical characterization of the wild type PCSK9/EGF(A B) complex and natural familial hypercholesterolemia mutants. *J Biol Chem* 284, 1313-1323.
15. Seidah N G (2009). PCSK9 as a therapeutic target of dyslipidemia. *Expert Opin Ther Targets* 13, 19-28.
16. Graham M J, Lemonidis K M, Whipple C P, Subramaniam A, Monia B P, Crooke S T, Crooke R M (2007). Antisense inhibition of proprotein convertase subtilisin/kexin type 9 reduces serum LDL in hyperlipidemic mice. *J Lipid Res* 48, 763-767.
17. Frank-Kamenetsky M, Grefhorst A, Anderson N N, Racie T S, Bramlage B, Akinc A, Butler D, Charisse K, Dorkin R, Fan Y, Gamba-Vitalo C, Hadwiger P, Jayaraman M, John M, Jayaprakash K N, Maier M, Nechev L, Rajeev K G, Read T, Röhl I, Soutschek J, Tan P, Wong J, Wang G, Zimmermann T, de Fougerolles A, Vornlocher H P, Langer R, Anderson D G, Manoharan M, Koteliansky V, Horton J D, Fitzgerald K (2008). Therapeutic RNAi targeting PCSK9 acutely lowers plasma cholesterol in rodents and LDL cholesterol in nonhuman primates. *Proc Natl Acad Sci USA* 105, 11915-11920.
18. Piper D, Jackson S, Liu Q, Romanow W, Shetterly S, Thibault S, Shan B, Walker N (2007). The Crystal Structure of PCSK9: A Regulator of Plasma LDL-Cholesterol. *Structure* 15, 545-552.
19. Cunningham D, Danley D E, Geoghegan K F, Matthew C Griffor M C, Hawkins J L, Subashi T A, Varghese A H, Ammirati M J, Culp J S, Hoth L R, Mansour M N, McGrath K M, Seddon A P, Shenolikar S, Stutzman-Engwall K J, Warren L C, Xia D, Qiu X (2007). Structural and biophysical studies of PCSK9 and its mutants linked to familial hypercholesterolemia. *Nature Struc Mol Biol* 14, 413-419.
20. Seidah N, Benjannet S, Wickham L, Marcinkiewicz J, Jasmin S, Stifani S, Basak A, Prat A, Chrétien M (2003). The secretory proprotein convertase neural apoptosis-regulated convertase 1 (NARC-1) liver regeneration and neuronal differentiation. *Proc Natl Acad Sci USA* 100, 928-933.
21. McNutt M C, Kwon H J, Chen C, Chen J R, Horton J D, Lagace T A (2009). Antagonism of secreted PCSK9 increases low density lipoprotein receptor expression in HepG2 cells. *J Biol Chem* 284, 10561-10570.
22. Swergold G, Biedermann S, Renard R, Nadler D, Wu R; Mellis S (2010). Safety, Lipid, and Lipoprotein Effects of REGN727/SAR236553, a Fully-Human Proprotein Convertase Subtilisin Kexin 9 (PCSK9) Monoclonal Antibody Administered Intravenously to Healthy Volunteers. *Circulation* 122, A23251.
23. Dias C, Shaywitz A, Smith B, Emery M, Bing G, Gibbs J, Wishner B, Stolman D, Crispino C, Cook B, Colbert A, Retter M, Xu R (2011). A Phase 1, Randomized, Double-Blind, Placebo-Controlled, Ascending Single Dose Study to Evaluate the Safety, Tolerability and Pharmacodynamics of AMG145. *Circulation* 124.
24. Amgen (2010) Ascending Multiple Dose Study to Evaluate the Safety, Tolerability, Pharmacokinetics and Pharmacodynamics of AMG 145 in Subjects With Hyperlipidemia on Stable Doses of a Statin. ClinicalTrails.Gov.
25. Crunkhorn S (2012). PCSK9 antibody reduces LDL cholesterol. *Nature Rev Drug Disc* 11, 11.

What is claimed is:

1. A method for treating hypercholesterolemia, and/or at least one symptom of dyslipidemia, atherosclerosis, CVD or coronary heart disease in a patient in need of said treatment, the method comprising administering to said patient a therapeutically effective amount of a compound of the formula:

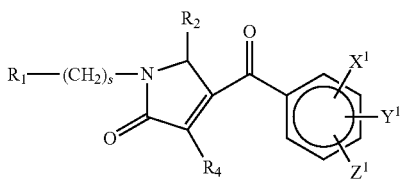

wherein $R_1$ is selected from the group of optionally substituted cycloalkyl, cycloalkyloxy, aryloxy, aralkoxy, heterocycle, heterocycloalkoxy, heteroaryl, and heteroaralkoxy;

$R_2$ is selected from the group of H and optionally substituted lower alkyl, cycloalkyl, aryl, heterocycle, and heteroaryl;

$R_4$ is selected from the group of H, lower alkyl, OH, SH, $NH_2$, halo, CN, carboxyl, and carboxamido;

wherein $X^1$ and $Y^1$ and are the same or different and each represents hydrogen, or a lower alkyl substituent and $Z^1$ is substituted at the para-position of the phenyl ring of said formula, and $Z^1$ represents an alkoxy substituent in which the alkyl moiety of said alkoxy substituent is substituted with an optionally substituted aryl group; and s is an integer from 1 to 4;

or a pharmaceutically acceptable salt or stereoisomer of said compound.

2. The method of claim 1, wherein the alkyl moiety of said alkoxy substituent is selected from the group consisting of benzyl, 2-methyl benzyl, 3-methyl benzyl and phenethyl.

3. A method for treating hypercholesterolemia, and/or at least one symptom of dyslipidemia, atherosclerosis, CVD or coronary heart disease in a patient in need of said treatment, the method comprising administering to said patient a therapeutically effective amount of a compound selected from the group consisting of:

4-[4-(benzyloxy)-3-methylbenzoyl]-3-hydroxy-1-[3-(morpholin-4-yl)propyl]-5-(pyridin-4-yl)-2,5-dihydro-1H-pyrrol-2-one (SBC-115,076)

3-hydroxy-4-{4-[(3-methylphenyl)methoxy]benzoyl}-1-[3-(morpholin-4-yl)propyl]-5-(pyridin-4-yl)-2,5-dihydro-1H-pyrrol-2-one (SBC-115,177)

4-[4-(benzyloxy)-2-methylbenzoyl]-3-hydroxy-1-[3-(morpholin-4-yl)propyl]-5-(pyridin-3-yl)-2,5-dihydro-1H-pyrrol-2-one (SBC-115,178)

4-[4-(benzyloxy)-3-methylbenzoyl]-3-hydroxy-1-[3-(morpholin-4-yl)propyl]-5-(pyridin-3-yl)-2,5-dihydro-1H-pyrrol-2-one (SBC-115,181)

4-[4-(benzyloyx)-2-methylbenzoyl]-3-hydroxy-1-[3-(morpholin-4-yl)propyl]-5-(pyridine-4-yl)-2,5-dihydro-1H-pyrrol-2-one (SBC-115,180), or a pharmaceutically acceptable salt or stereoisomer of said compound.

4. The method of claim 3, wherein said compound is 4-[4-(benzyloxy)-3-methylbenzoyl]-3-hydroxy-1-[3-(morpholin-4-yl)propyl]-5-(pyridin-4-yl)-2,5-dihydro-1H-pyrrol-2-one (SBC-115,076):

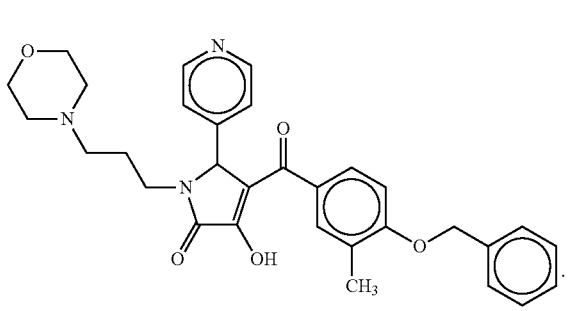

5. The method of claim 1, wherein the compound administered is a compound of said formula wherein $R_1$ is selected from the group consisting of optionally substituted heterocycle and heteroaryl and s is 3.

* * * * *